(12) United States Patent
Kosel et al.

(10) Patent No.: US 11,859,491 B2
(45) Date of Patent: Jan. 2, 2024

(54) LOW POWER WATER CUT SENSING

(71) Applicant: KING ABDULLAH UNIVERSITY OF SCIENCE AND TECHNOLOGY, Thuwal (SA)

(72) Inventors: Jürgen Kosel, Thuwal (SA); Altynay Kaidarova, Thuwal (SA); Abdullah Saud Almansouri, Thuwal (SA); Mohammed Asadullah Khan, Thuwal (SA); Liam Swanepoel, Stellenbosch (ZA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 622 days.

(21) Appl. No.: 17/043,177

(22) PCT Filed: Apr. 4, 2019

(86) PCT No.: PCT/IB2019/052770
§ 371 (c)(1),
(2) Date: Sep. 29, 2020

(87) PCT Pub. No.: WO2019/197949
PCT Pub. Date: Oct. 17, 2019

(65) Prior Publication Data
US 2021/0054739 A1    Feb. 25, 2021

Related U.S. Application Data

(60) Provisional application No. 62/654,681, filed on Apr. 9, 2018.

(51) Int. Cl.
*E21B 49/08* (2006.01)
*G01N 27/02* (2006.01)
(Continued)

(52) U.S. Cl.
CPC ....... *E21B 49/0875* (2020.05); *G01N 27/023* (2013.01); *G01N 29/032* (2013.01);
(Continued)

(58) Field of Classification Search
CPC .... E21B 49/0875; E21B 49/08; E21B 49/088; E21B 49/087; G01N 2291/0226;
(Continued)

(56) References Cited

U.S. PATENT DOCUMENTS

| | | | |
|---|---|---|---|
| 5,129,262 A * | 7/1992 | White | G01P 15/08 310/313 R |
| 8,521,451 B2 * | 8/2013 | Kong | G01N 33/2847 702/50 |
| 2016/0334343 A1 * | 11/2016 | Hurlimann | E21B 49/08 |

FOREIGN PATENT DOCUMENTS

JP         2014057289 A  *  3/2014  .........  H01S 3/10015

OTHER PUBLICATIONS

Al-Shalabi, E.W., et al., "A Comprehensive Review of Low Salinity/Engineered Water Injections and Their Applications in Sandstone and Carbonate Rocks," Journal of Petroleum Science and Engineering, Dec. 21, 2015, vol. 139, pp. 137-161, ELSEVIER.
(Continued)

*Primary Examiner* — Feba Pothen
*Assistant Examiner* — James Split
(74) *Attorney, Agent, or Firm* — PATENT PORTFOLIO BUILDERS, PLLC (57) ABSTRACT

A system for determining a water cut of a water/oil emulsion includes a water cut sensor with a magnetoelastic ribbon, an inductive coil arranged proximate to the magnetoelastic ribbon so that an electromagnetic field produced by the inductive coil electromagnetically excites the magnetoelastic ribbon, and an alternating current source. A processor is configured to determine the water cut of the water/oil
(Continued)

emulsion based on a resonant frequency of the magnetoelastic ribbon while the magnetoelastic ribbon is excited by the inductive coil. A feed line is coupled to the water cut sensor. The feed line includes an electrical coupling between the alternating current source and the inductive coil of the water cut sensor. The feedline includes an electrical coupling between the processor and the inductive coil of the water cut sensor or the processor is coupled to an acoustic sensor.

19 Claims, 3 Drawing Sheets

(51) Int. Cl.
  *G01N 29/032* (2006.01)
  *G01N 29/036* (2006.01)
  *G01N 29/24* (2006.01)
  *G01N 33/28* (2006.01)

(52) U.S. Cl.
  CPC ....... *G01N 29/036* (2013.01); *G01N 29/2412* (2013.01); *G01N 33/2847* (2013.01); *G01N 2291/0226* (2013.01); *G01N 2291/0228* (2013.01); *G01N 2291/02433* (2013.01)

(58) Field of Classification Search
  CPC . G01N 2291/0228; G01N 2291/02433; G01N 27/023; G01N 29/036; G01N 29/2412; G01N 33/2847; G01N 29/032
  See application file for complete search history.

(56) References Cited

OTHER PUBLICATIONS

Grimes, C.A., et al., "Magnetoelastic Sensors for Remote Query Environmental Monitoring," Smart Materials and Structures, 1999, vol. 8, No. 5, pp. 639-646.
Grimes, C.A., et al., "Theory, Instrumentation and Applications of Magnetoelastic Resonance Sensors: A Review," Sensors, Mar. 2, 2011, vol. 11, pp. 2809-2844.
Grimes, C.A., et al., "Wireless Magnetoelastic Resonance Sensors: A Critical Review," Sensors, Jul. 23, 2002, vol. 2, pp. 294-313.
International Search Report in corresponding/related International Application No. PCT/IB2019/052770, dated Jul. 2, 2019.
Jain, M.K., et al., "Magneto-Acoustic Sensors for Measurement of Liquid Temperature, Viscosity and Density," Applied Acoustics, Aug. 2001, vol. 62, pp. 1001-1011, ELSEVIER.
Written Opinion of the International Searching Authority in corresponding/related International Application No. PCT/IB2019/052770, dated Jul. 2, 2019.

\* cited by examiner

LOW POWER WATER CUT SENSING

CROSS-REFERENCE TO RELATED APPLICATIONS

This application is a U.S. National Stage Application of International Application No. PCT/IB2019/052770, filed on Apr. 4, 2019, which claims priority to U.S. Provisional Patent Application No. 62/654,681, filed on Apr. 9, 2018, entitled "MAGNETOLASTIC WATER CUT SENSOR," the disclosures of which are incorporated herein by reference in their entirety.

BACKGROUND

Technical Field

Embodiments of the subject matter disclosed herein generally relate to systems and methods for sensing water cut of a water/oil emulsion with low energy consumption.

Discussion of the Background

Efficient well performance in the oil and gas industry is optimized using various sensors that monitor production parameters including multiphase flow rates and contactless water fraction of produced hydrocarbons, also known as water cut. Technical advances in electronics, low-power sensors and wireless communications have enabled a paradigm shift in wireless monitoring and control for a wide range of applications in the oil and gas industry. The abundance of remote and hazardous locations in the industry has fueled a growing demand for remote sensor applications. Downhole measurements are challenging because the metering hardware must be designed to withstand the harsh downhole conditions, where hydrostatic pressure and temperature can reach 30,000 PSI and more than 230° C., respectively. Downhole measurement does, however, mean that the gas phase may not be present in the mixture, due to the high pressure; thereby, potentially simplifying the system design.

Real-time monitoring through inline water cut sensors allows for efficient reservoir management and production allocation. Conventional water cut sensors are either costly, heavy, intrusive, severely sensitive to water salinity, or incapable of covering the full range of possible water cuts. Inline detection of water fraction in oil can be done by sensing the differences in viscosity, effective electric permittivity, or IR/gamma-ray absorption characteristics of oil/water mixtures. Electrical sensors based on capacitive measurements or radio frequency resonator measurements (s-parameters) are two different approaches that can be used to analyze the water cut of emulsions by measuring the impedance of the emulsion. A commercially available water cut sensor, like the sensor produced by Delta-C (DC-1510 Series), is based on the capacitance measurement of the oil/water mixture, which can cover a limited water range. Even though this approach offers high accuracy, it is not applicable nor reliable for water cut measurements above 50%, due to a short circuit effect between the capacitor electrodes after inversion.

Another common method for measuring the phase fraction is to transmit gamma rays through the production mixture and analyze the energy attenuation. As radioactive materials are required to produce gamma rays, gaining regulatory permits for this sensor type as well as the handling and later disposal of the radioactive materials strongly affects the employment of this technology. The use of X-rays for phase fraction measurements presents similar complications.

Saudi Aramco developed a water cut sensor that operates based on the difference in densities of oil and water, which affects the acoustic speeds of sound traveling through it. This method has the advantages of being nonintrusive to allow full bore access. Although it works in the 0%-100% water-cut range, flow loop reference measurements show an error of 5%, exceeding the accuracy required for production and reservoir management uses.

Thus, there is a need for systems and methods for determining water cut of a water/oil emulsion that is accurate over a wide water cut range and that does not involve radioactive energy.

SUMMARY

According to an embodiment, there is a system for determining a water cut of a water/oil emulsion, the system including a water cut sensor with a magnetoelastic ribbon and an inductive coil arranged proximate to the magnetoelastic ribbon so that an electromagnetic field produced by the inductive coil electromagnetically excites the magnetoelastic ribbon. The inductive coil is operated by an alternating current source. A processor is configured to determine the water cut of the water/oil emulsion based on a resonant frequency of the magnetoelastic ribbon while the magnetoelastic ribbon is excited by the electromagnetic field produced by the inductive coil. A feed line is coupled to the water cut sensor. The feed line includes an electrical coupling between the alternating current source and the inductive coil of the water cut sensor. The feedline includes an electrical coupling between the processor and the inductive coil of the water cut sensor or the processor is coupled to an acoustic sensor.

According to another embodiment, there is a method for determining a water cut of a water/oil emulsion. A water cut sensor is arranged in the water/oil emulsion. The water cut sensor comprises a magnetoelastic ribbon and an inductive coil arranged proximate to the magnetoelastic ribbon so that an electromagnetic field produced by the inductive coil electromagnetically excites the magnetoelastic ribbon. The magnetoelastic ribbon is electromagnetically excited by the electromagnetic field produced by the inductive coil. The water cut of the water/oil emulsion is determined based on a resonant frequency of the magnetoelastic ribbon while the magnetoelastic ribbon is electromagnetically excited.

According to a further embodiment, there is a method of producing a system for determining a water cut of a water/oil emulsion. A water cut sensor comprising a magnetoelastic ribbon and an inductive coil arranged proximate to the magnetoelastic ribbon so that an electromagnetic field produced by the inductive coil electromagnetically excites the magnetoelastic ribbon is provided. The water cut sensor is coupled to a feed line. An alternating current source is coupled to the inductive coil via the feed line. A processor is coupled to the inductive coil via the feedline or is coupled to an acoustic sensor. The processor is configured to determine the water cut of the water/oil emulsion based on a resonant frequency of the magnetoelastic ribbon.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of a water cut sensor.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1A:
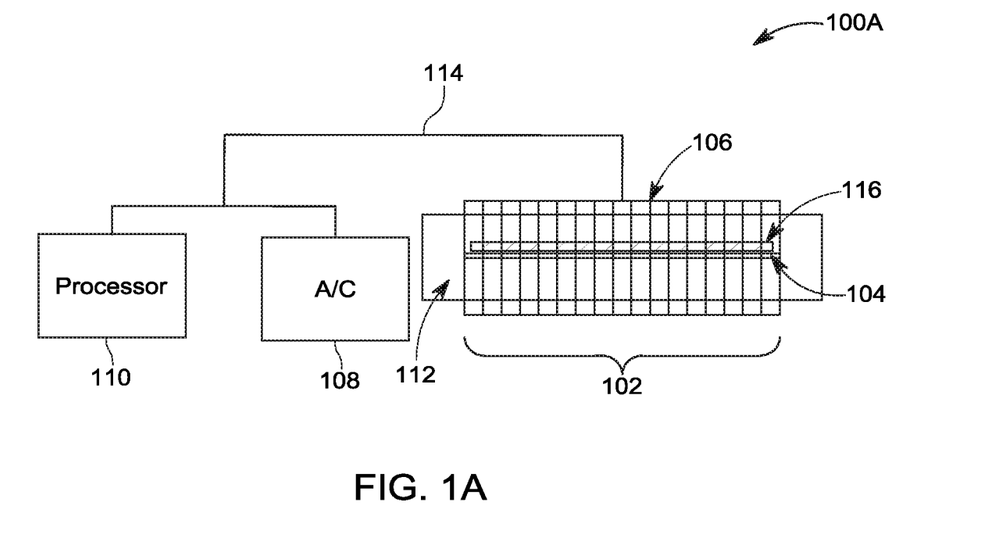
FIGS. 1A and 1B are schematic diagrams of systems for determining water cut according to embodiments.
Figure 1B:
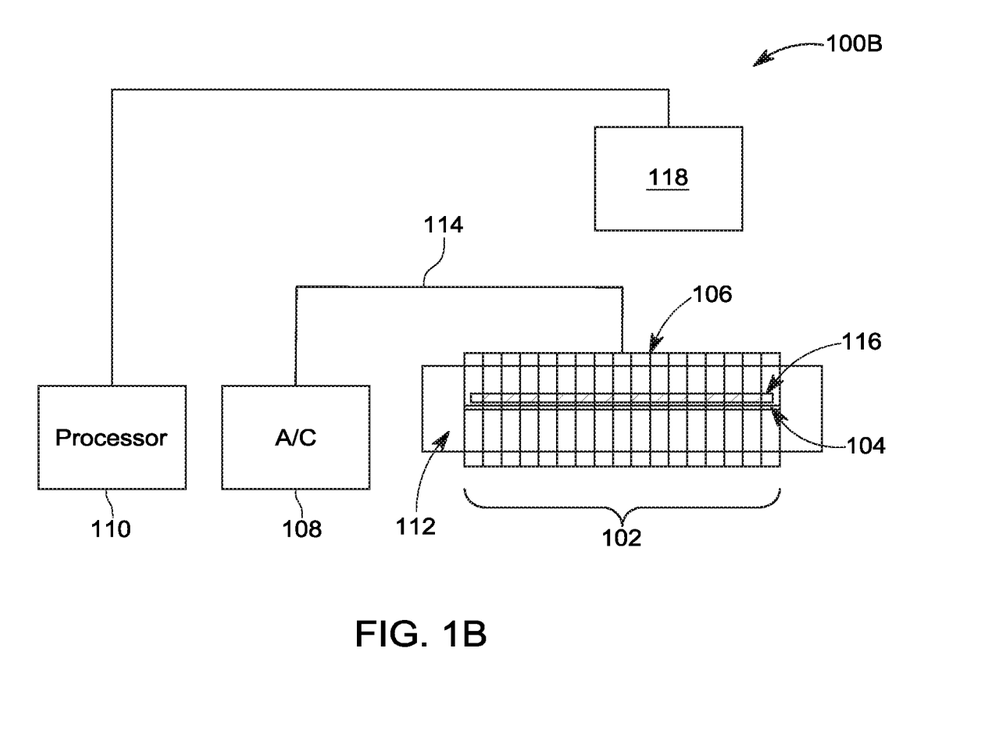

FIGS. 1A and 1B are schematic diagrams of systems for determining water cut according to embodiments. The systems 100A and 100B include a water cut sensor 102 comprising a magnetoelastic ribbon 104 and an inductive coil 106 arranged proximate to the magnetoelastic ribbon 104 so that an electromagnetic field produced by the inductive coil 106 electromagnetically excites the magnetoelastic ribbon 104. The proximate arrangement can involve the inductive coil 106 surrounding the magnetoelastic ribbon 104 (as illustrated in FIGS. 1A and 1B) or the inductive coil can be arranged adjacent to the magnetoelastic ribbon 104. The systems also include an alternating current source 108 and a processor 110 configured to determine the water cut of the water/oil emulsion 112 based on a resonant frequency of the magnetoelastic ribbon 104 while the magnetoelastic ribbon 104 is excited by electromagnetic field produced by the inductive coil. A feed line 114 is coupled to the water cut sensor 102. The feed line 114 includes an electrical coupling between the alternating current source 108 and the inductive coil 106 of the water cut sensor 102. The feedline includes an electrical coupling between the processor 110 and the inductive coil 106 of the water cut sensor 102 (FIG. 1A) or the processor 110 is coupled to an acoustic sensor 118 (FIG. 1B). Those skilled in the art will recognize that an acoustic sensor refers to a structure comprising hardware for receiving acoustic waves and measuring the frequency of the received acoustic waves.

As also illustrated in FIGS. 1A and 1B, a magnetic biasing ribbon 116 is arranged adjacent to the magnetoelastic ribbon 104. The magnetic biasing ribbon 116 magnetizes the magnetoelastic ribbon, thereby reducing the required excitation field strength and increasing the impedance response in the inductive coil 106. The water cut sensor 102 can be arranged in a housing that is lowered into the downhole. The housing protects the components of the water cut sensor 102 from being impinged upon by anything other than the water/oil emulsion because such an impingement can affect the resonant frequency of the magnetoelastic ribbon.

As will be discussed in more detail below, the sensor 102 operates so that when it is immersed in a water/oil emulsion, the resonant frequency of the magnetoelastic ribbon 104 changes depending upon the water cut of the emulsion. This change in the resonant frequency of the magnetoelastic ribbon 104 in turn induces changes in the resonant frequency and vibration amplitude of the impedance of the inductive coil 106. Thus, the water cut of a water/oil emulsion can be determined based on a resonant frequency of the magnetoelastic ribbon 104, which in turn can be determined based on a measured shift in the resonant frequency and/or vibration amplitude of the impedance of the inductive coil 106. Alternatively, the resonant frequency of the magnetoelastic ribbon 104 can be determined using an acoustic sensor, which measures sound waves generated by the magnetoelastic ribbon 104.

The processor 110 can be any type of processor suitable programmed to determine the resonant frequency or the vibration amplitude of the impedance of the inductive coil 106 in the manner described in more detail below. Thus, the processor 110 can be coupled to a memory that stores the programming for the processor. The memory can be integrated into the processor 110 or can be a separate memory. Further, the processor can include an integrated analog-to-digital converter to convert the analog measurements into a suitable digital form, or a separate analog-to-digital converter can be coupled between the processor 110 and the inductive coil 106.

The sensor 102 of the water cut system 100 was produced to evaluate its performance. The magnetoelastic ribbon 104 comprised an iron-based alloy, which during testing was the Ultra-Stripe® produced by Sensormatic, and had dimensions 36×6×0.028 mm³. The magnetic biasing ribbon 116 comprised iron and nickel and had dimensions of 30×6×0.05 mm³. The alternating current source 108 produced frequencies between 50 kHz and 62 kHz, which covered the relevant frequency range that included the resonance peak of 58 kHz of the magnetoelastic ribbon 104. It should be recognized that the dimensions of the ribbons, resonant frequency, and frequency range mentioned above are provided as examples and that these ribbons can be employed with the disclosed embodiments having different dimensions, different resonant frequencies, and different frequency ranges. In general, a decrease in the ribbon geometry increases the ribbon resonant frequency and vice-versa.

The impedance measured in the inductive coil 106 is affected by the magnetic susceptibility of the core materials, which includes the magnetoelastic ribbon 104, the magnetic biasing ribbon 116, and the water/oil emulsion. The impedance of the inductive coil is given as $Z=R+jX_L$, where the reactance $X_L=\omega L$, and the inductance L of the coil can be written as:

$$L = \frac{N^2 \mu(f, \eta) A}{l} \quad (1)$$

where N represents the amount of turns in the coil (350 in the tested system), l the length (12.6 m in the tested system) and A the cross-sectional area of the inductor (6 mm² in the tested system). Furthermore, the permeability of the core material (μ) is influenced by the water/oil liquid volume inside the sensor and the permeability of the magnetoelastic ribbon 104 and the magnetic biasing ribbon 116. The change in core material permeability induced by changing the liquid from pure water to pure crude is significantly smaller than the fluctuations measured in the sensor material and therefore were ignored. The permeability of the magnetoelastic ribbon 104 is a function of frequency f and the surrounding medium's viscosity η through magnetostriction.

Magnetoelastic vibrations in a magnetoelastic sensor occur, when the applied magnetic field is time varying in nature, causing the field-generated strain to vary with time; thus, producing a longitudinal elastic wave. These vibrations, in turn, generate a secondary magnetic field in the inductive coil that can be detected. The measured shift in resonant frequency and/or vibration amplitude of the impedance of the inductive coil is caused by a change in the material surrounding the magnetoelastic ribbon 104, i.e., a change in the water cut of the water/oil emulsion in which the water cut sensor 102 is submerged.

Figure 2:
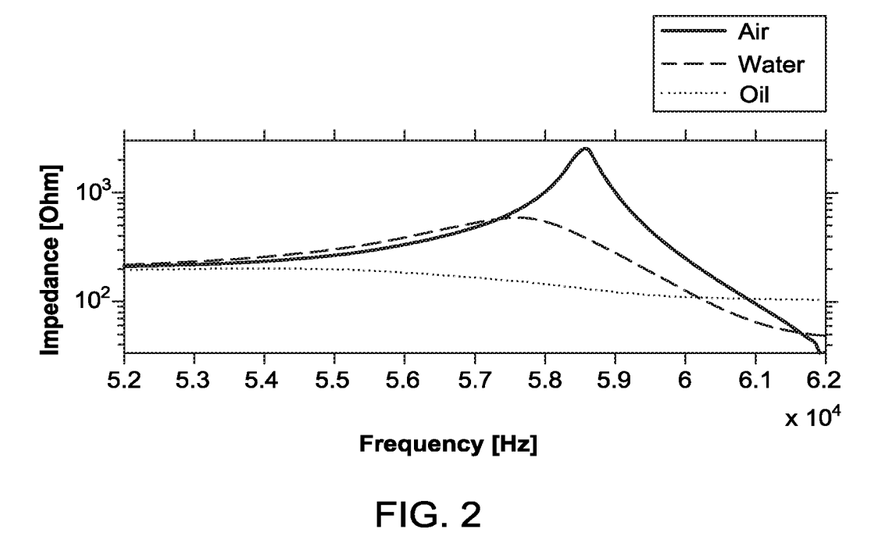
FIG. 2 is a graph of the response of a water cut sensor to oil, water, and air according to embodiments.

The resonant frequency of the magnetoelastic ribbon is determined by the effective damping force induced by the viscosity of the surrounding medium. Therefore, magnetoelastic ribbons in mediums of varying viscosity possess a significantly different characteristic frequency response. The impedance of the inductive coil with the amorphous and bias ribbons was measured for air, water and oil, the results of which are illustrated in FIG. 2. As illustrated in the graph of FIG. 2, there was a reduction in resonant frequency and vibration amplitude from exposure in air to water of 0.99 kHz and 1.93 kΩ, respectively. Further reductions with exposure to oil were measured at 3.37 kHz and 0.4 kΩ from the measured peaks in water. Thus, the water cut sensor 102 exhibited amplitude changes of 75% and 90% when the water cut sensor 102 is loaded in water and oil respectively, compared to the water cut sensor when it is unloaded in air. Further, the water cut sensor 102 exhibited frequency changes of 0.46% and 3.88% when the water cut sensor 102 is loaded in water and oil respectively, compared to the water cut sensor when it is unloaded in air. With a measurement voltage of 10 mV, the power consumption was 40 nW in air. When immersed in the water/oil emulsion this value ranges from 160 nW to 500 nW. As will be appreciated, power consumption in these ranges characterizes the water cut sensor 102 as an ultra-low-power sensor.

Figure 3:
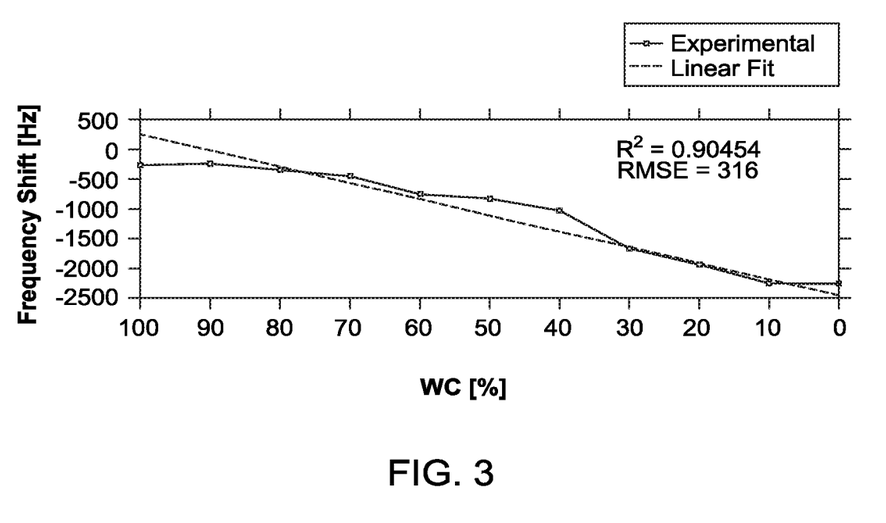
FIG. 3 is a graph of the frequency shift of the resonant frequency of an inductive coil's impedance response of a water cut sensor to different water cuts according to embodiments.

The water cut response of the water cut sensor 102 was further evaluated by immersing the sensor in water/oil emulsions having different water cuts and measuring the resonant frequency shift of the impedance of the inductive coil 106, which provides both a resonant frequency and a vibration amplitude. Stable water/oil emulsions were created with 10% volumetric surfactant (Tween 20). Different magnetoelastic ribbons 104 were used with each of the different water cut emulsions, thereby ensuring that there were no liquids present on the surface of the magnetoelastic ribbon 104 before immersing it in a particular water/oil emulsion. Each magnetoelastic ribbon was characterized in air, whereafter the frequency and impedance shifts were normalized to the frequency shift caused by 100% water. The results of this testing is illustrated in the graph of FIG. 3. As illustrated, as the water cut of the oil/water emulsion decreased, there was a decrease in resonant frequency (relative to an undamped sensor) of the inductive coil 106. This is consistent with the following formula for calculating the relative change in resonant frequency:

$$\Delta f = \frac{\sqrt{\pi f_o}}{2\pi \rho_s d} \sqrt{\eta \rho_l} \quad (2)$$

where $f_o$, the resonant frequency of the ribbon in vacuum, $\rho_s$ and d the density and thickness of the ribbon, respectively, and η and $\rho_l$ the effective dynamic viscosity and density of the surrounding medium, respectively. The frequency shift is proportional to the square root of the medium's viscosity and density product.

These experimental results were consistent with the prediction models considered in the evaluation, which indicates that the evaluated sensor possessed a sensitivity to a reduction or increase of the density/viscosity product. The sensitivity was approximated as 27 Hz/% by fitting a linear function within the 90-10% WC range. These experimental results also support a determination that the water cut sensor is surrounded by an air/gas mixture when the resonant frequency is lower than a resonant frequency corresponding to 90% water cut.

Because the water cut sensor 102 is designed to be used in very harsh conditions, sometimes with brine salinity ranging from thousands to 260,000 ppm, the magnetoelastic ribbon 104 and the magnetic biasing ribbon 116 can corrode, which can affect their magnetic properties. In order to avoid or minimize corrosion, the magnetoelastic ribbon 104 and the magnetic biasing ribbon 116 can be provided with a non-corrosive coating. For example, the magnetoelastic ribbon 104 and the magnetic biasing ribbon 116 can be dipped in a non-corrosive coating, such as polytetrafluoroethylene (PTFE) (known under the tradename Teflon®), parylene C, and the like. When the magnetoelastic ribbon 104 and the magnetic biasing ribbon 116 were dip coated in polytetrafluoroethylene, the ribbons were coated on both sides and the coating added approximately 2.5 μm in thickness to each ribbon. Thus, the tested magnetoelastic ribbon, including the coating, was only 28 μm thick. Testing with this coating showed that the saturation magnetization of the magnetoelastic ribbon 104 and the magnetic biasing ribbon 116 remained stable in air, water, and oil over twenty days of testing. The non-corrosive coating caused the resonant frequency of the magnetoelectric ribbon to drop by ~3%, which is due to the mass loading the coating causes to the vibrating body. This value is near the theoretical value of 2.13%. With the coating applied, the resonant frequencies of the inductive coil 106 remained constant in air, water, and oil for an extended period of time.

Figure 4:
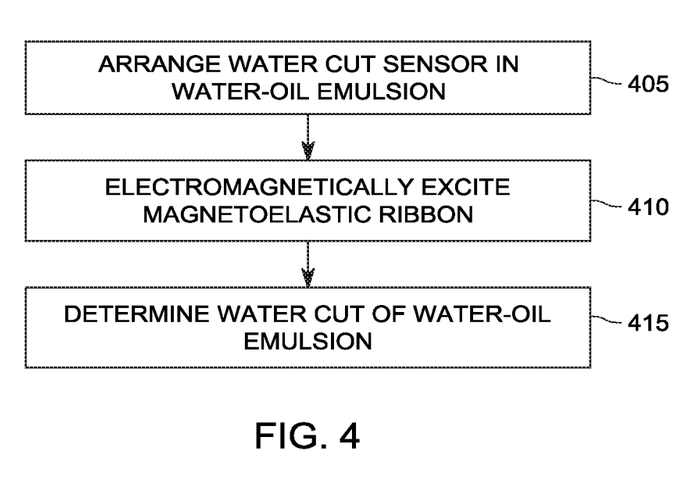
FIG. 4 is a flowchart of a method for determining water cut according to embodiments.

FIG. 4 is a flowchart of a method for determining water cut according to embodiments. A water cut sensor 102 is arranged in the water/oil emulsion 112 (step 405). The water cut sensor 102 comprises a magnetoelastic ribbon 104 and an inductive coil 106 arranged proximate to the magnetoelastic ribbon 104 so that an electromagnetic field produced by the inductive coil 106 electromagnetically excites the magnetoelastic ribbon 104. The magnetoelastic ribbon 104 is then electromagnetically excited by the electromagnetic field produced by the inductive coil 106 (step 410). The water cut of the water/oil emulsion 112 is determined based on a resonant frequency of the magnetoelastic ribbon 104 while the inductive coil 106 is electromagnetically excited (step 415). The resonant frequency of the magnetoelastic ribbon 104 can be detected electromagnetically or acoustically. Electromagnetically detecting the resonant frequency can be achieved by detecting the secondary magnetic field in the inductive coil 106 generated by vibrations of the magnetoelastic ribbon 104. Acoustically detecting the resonant frequency can be achieved using an acoustic sensor to acoustically measure sound waves generated by the elastic vibrations in the magnetoelastic ribbon 104.

The determination of the water cut of the water/oil emulsion can involve determining the resonant frequency or vibration amplitude of the impedance of the inductive coil while the inductive coil is electromagnetically excited and identifying, using a table correlating resonant frequencies or vibration amplitudes of the impedance of the inductive coil and water cut, the water cut based on the determined resonant frequency or vibration amplitude of the impedance of the inductive coil. The resonant frequency and/or vibration amplitude is detected electromagnetically. The table correlating resonant frequencies or the vibration amplitudes of the impedance of the inductive coil and water cut is generated by exposing the water cut sensor to a plurality of water/oil emulsions having different water cuts, determining the resonant frequency or the vibration amplitude of the impedance of the inductive coil when the water cut sensor is exposed to the plurality of water/oil emulsions, and recording, in the table, the correlation between the resonant frequency or the vibration amplitude of the impedance of the inductive coil and the water cut of the corresponding one of the plurality of water/oil emulsions. Consistent with the graph in FIG. 3, this can involve make a number of measurements using different water cuts (e.g., in increments of 10%) and then using a linear fit to the measurement results to generate values for water cuts that were not directly measured, e.g., 49%, etc.

Figure 5:
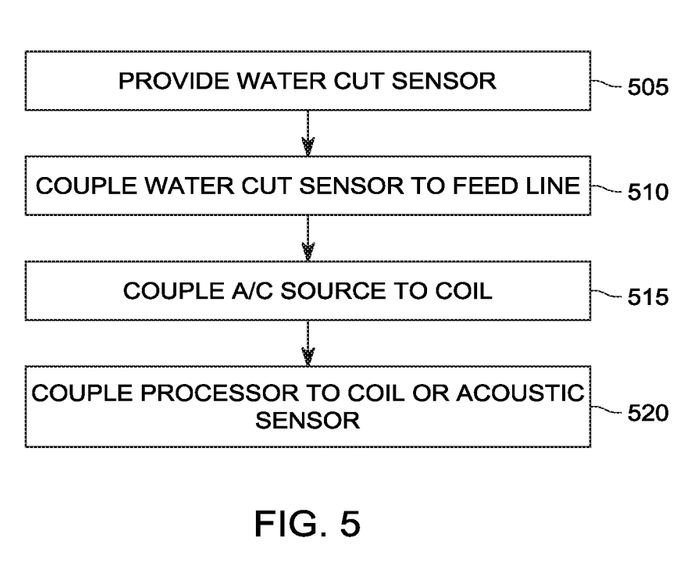
FIG. 5 is a flowchart of a method for producing a system for determining water cut according to embodiments.

FIG. 5 is a flowchart of a method for producing a system for determining water cut according to embodiments. Initially, a water cut sensor 102, which comprises a magnetoelastic ribbon 104 and an inductive coil 106 arranged proximate to the magnetoelastic ribbon 104 so that an electromagnetic field produced by the inductive coil electromagnetically excites the magnetoelastic ribbon, is provided (step 505). The water cut sensor 102 is coupled to a feed line 114 (step 510). An alternating current source 108 is coupled to the inductive coil 106 via the feed line 114 (step 515). A processor 110 is coupled to the inductive coil 106 via the feedline 114 or is coupled to an acoustic sensor 118 (step 520). The processor 110 is configured to determine the water cut of the water/oil emulsion 112 based on a resonant frequency of the magnetoelastic ribbon 104.

The method can further involve applying a protective coating on the magnetoelastic ribbon 104, for example, by dipping the magnetoelastic ribbon 104 in Polytetrafluoroethylene, PTFE. The method can also involve arranging a magnetic biasing ribbon 116 adjacent to the magnetoelastic ribbon 104. The method can further involve storing, in a memory associated with the processor 110, a table correlating resonant frequencies or vibration amplitudes of the impedance of the inductive coil and water cut.

The disclosed systems and methods for determining water cut are particularly advantageous because they provide a wireless capability and the ability to determine water cut with a very low power requirement. The wireless capability relates to the lack of contact between the inductive coil 106 and the magnetoelastic ribbon 104. Thus, the magnetoelastic ribbon 104 can be located inside a liquid-filled chamber/enclosure and the excitation and detection of the resonant frequency of the magnetoelastic ribbon 104 can be achieved with a coil (and wires) outside of the liquid-filled chamber/enclosure. Further, in a wireless implementation the processor 110, sensor 102, and a battery power supply may be positioned downhole. Enclosing these components in an environmental condition-proof enclosure downhole allows for downhole sampling and logging of water cut data without the need to run communication wires down the bore. The disclosed systems and methods are ultra-low power due to the fact that these sensor 102 consumes a minimum power of, for example, 500 nW, which is an extremely low power consumption for a water cut detector. Even with the additional power requirements of the processor 110 and any necessary amplifier/filter circuits, the systems 100A and 100B can be implemented using a battery supply.

The disclosed water cut sensor is scalable in size and, consequently, resonating frequency. Thus, it can be altered for a specific bore diameter or emulsion compositions, while avoiding frequency noise that may be present or providing multi-sensor encoded readout. The disclosed water cut sensor requires very little power, due to the low biasing field required to excite a signal from the sensor ribbon, which can be provided by an additional magnetized biasing ribbon. With a thickness of 28 μm the sensor ribbon is of very low mass and greatly affected by slight changes in surface damping caused by viscosity changes in the surrounding medium, making it adequately sensitive for water cut measurements.

The disclosed water cut sensor can detect all three phases (i.e., gas, water, and oil) with amplitude changes of 75% and 99% and resonant frequency shifts of 0.46% and 3.88%, respectively, compared to the gas phase. The response of the sensor enables characterizing the water-cut range from 10%-90%. Further, the anti-corrosion coating prevents decay of the magnetic characteristics and ensures long-lasting performance of the water cut sensor.

The disclosed embodiments provide a system for determining water cut of a water/oil emulsion. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A system for determining a water cut of a water/oil emulsion, the system comprising:
  a water cut sensor comprising a magnetoelastic ribbon and an inductive coil arranged proximate to the magnetoelastic ribbon so that an electromagnetic field produced by the inductive coil electromagnetically excites the magnetoelastic ribbon;
  an alternating current source;

a processor configured to determine the water cut of the water/oil emulsion based on a resonant frequency of the magnetoelastic ribbon while the magnetoelastic ribbon is excited by electromagnetic field produced by the inductive coil, wherein the processor is further configured to determine that the water cut sensor is surrounded by an air/gas mixture when the resonant frequency is lower than a resonant frequency corresponding to a 90% water cut; and a feed line coupled to the water cut sensor, wherein the feed line includes an electrical coupling between the alternating current source and the inductive coil of the water cut sensor, wherein the feed line includes an electrical coupling between the processor and the inductive coil of the water cut sensor or the processor is coupled to an acoustic sensor.

2. The system of claim 1, wherein the water cut sensor further comprises a magnetic biasing ribbon arranged adjacent to the magnetoelastic ribbon.

3. The system of claim 1, wherein the magnetoelastic ribbon includes a protective coating.

4. The system of claim 3, wherein the protective coating is polytetrafluoroethylene, PTFE.

5. The system of claim 1, wherein the water cut sensor further comprises a housing in which the magnetoelastic ribbon and inductive coil are arranged.

6. The system of claim 1, wherein the feedline includes the electrical coupling between the processor and the inductive coil, and the processor is configured to:

determine the water cut of the water/oil emulsion by determining a resonant frequency or a vibration amplitude of an impedance of the inductive coil when the alternating current source is applied to the inductive coil; and identify, using a table correlating resonant frequencies or vibration amplitudes of the impedance of the inductive coil and water cut, the water cut based on the determined resonant frequency or the determined vibration amplitude of the impedance of the inductive coil.

7. The system of claim 6, further comprising:

a memory, coupled to the processor, which stores the table.

8. The system of claim 1, wherein the system detects water cut ranging from 10%-90%.

9. A method for determining a water cut of a water/oil emulsion, the method comprising:

arranging a water cut sensor in the water/oil emulsion, wherein the water cut sensor comprises a magnetoelastic ribbon and an inductive coil arranged proximate to the magnetoelastic ribbon so that an electromagnetic field produced by the inductive coil electromagnetically excites the magnetoelastic ribbon;

electromagnetically exciting the magnetoelastic ribbon by the electromagnetic field produced by the inductive coil;

determining the water cut of the water/oil emulsion based on a resonant frequency of the magnetoelastic ribbon while the magnetoelastic ribbon is electromagnetically excited; and determining that the water cut sensor is surrounded by an air/gas mixture when the resonant frequency is lower than a resonant frequency corresponding to a 90% water cut.

10. The method of claim 9, wherein the determination of the water cut of the water/oil emulsion based on the resonant frequency of the magnetoelastic ribbon comprises:

determining a resonant frequency or vibration amplitude of an impedance of the inductive coil while the magnetoelastic ribbon is electromagnetically excited;

identifying, using a table correlating resonant frequencies or vibration amplitudes of the impedance of the inductive coil and water cut, the water cut based on the determined resonant frequency or vibration amplitude of the impedance of the inductive coil.

11. The method of claim 10, wherein the resonant frequency or vibration amplitude is detected electromagnetically.

12. The method of claim 10, wherein the table correlating resonant frequencies or the vibration amplitudes of the impedance of the inductive coil and water cut is generated by:

exposing the water cut sensor to a plurality of water/oil emulsions having different water cuts;

determining the resonant frequency or the vibration amplitude of the impedance of the inductive coil when the water cut sensor is exposed to the plurality of water/oil emulsions; and recording, in the table, the correlation between the resonant frequency or the vibration amplitude of the impedance of the inductive coil and the water cut of the corresponding one of the plurality of water/oil emulsions.

13. The method of claim 12, further comprising:

generating a linear fit of the determined resonant frequencies or vibration amplitudes of the impedance of the inductive coil; and recording, in the table, water cut values for water cuts that the water cut sensor were not exposed to using the linear fit.

14. The method of claim 9, wherein the resonant frequency of the inductive coil decreases as the water cut increases.

15. A method of producing a system for determining a water cut of a water/oil emulsion, the method comprising:

providing a water cut sensor comprising a magnetoelastic ribbon and an inductive coil arranged proximate to the magnetoelastic ribbon so that an electromagnetic field produced by the inductive coil electromagnetically excites the magnetoelastic ribbon;

coupling the water cut sensor to a feed line;

coupling an alternating current source to the inductive coil via the feed line;

coupling a processor to the inductive coil via the feedline or coupling the processor to an acoustic sensor, wherein the processor is configured to determine the water cut of the water/oil emulsion based on a resonant frequency of the magnetoelastic ribbon, wherein the processor is further configured to determine that the water cut sensor is surrounded by an air/gas mixture when the resonant frequency is lower than a resonant frequency corresponding to a 90% water cut.

16. The method of claim 15, further comprising:

applying a protective coating on the magnetoelastic ribbon.

17. The method of claim 16, wherein the application of the protective coating comprises:

dipping the magnetoelastic ribbon in Polytetrafluoroethylene, PTFE.

18. The method of claim 15, further comprising:

arranging a magnetic biasing ribbon adjacent to the magnetoelastic ribbon.

19. The method of claim 15, further comprising:
storing, in a memory associated with the processor, a table correlating resonant frequencies or vibration amplitudes of an impedance of the inductive coil and water cut.

* * * * *